United States Patent
Rimbach et al.

(10) Patent No.: US 9,304,092 B2
(45) Date of Patent: Apr. 5, 2016

(54) APPARATUS FOR EXAMINING TEST BODIES

(71) Applicants: Jan Rimbach, Erfurt (DE); Kirke Rimbach, Bad Tennstedt (DE)

(72) Inventors: Jan Rimbach, Erfurt (DE); Kirke Rimbach, Bad Tennstedt (DE)

(73) Assignee: MatriX Technologies GmbH, Feldkirchen (DE)

( * ) Notice: Subject to any disclaimer, the term of this patent is extended or adjusted under 35 U.S.C. 154(b) by 196 days.

(21) Appl. No.: 14/028,445

(22) Filed: Sep. 16, 2013

(65) Prior Publication Data
US 2014/0079183 A1    Mar. 20, 2014

(30) Foreign Application Priority Data
Sep. 18, 2012   (DE) .......................... 10 2012 216 687

(51) Int. Cl.
| G01N 23/04 | (2006.01) |
| G01N 23/08 | (2006.01) |
| G01N 23/083 | (2006.01) |
| G01N 23/087 | (2006.01) |
| G01N 23/02 | (2006.01) |

(52) U.S. Cl.
CPC .............. *G01N 23/083* (2013.01); *G01N 23/02* (2013.01); *G01N 23/04* (2013.01); *G01N 23/08* (2013.01); *G01N 23/087* (2013.01)

(58) Field of Classification Search
CPC ..... G01N 23/04; G01N 23/08; G01N 23/083; G01N 23/087; A61B 17/62
USPC .................................... 378/208, 209, 53–58
See application file for complete search history.

(56) References Cited

U.S. PATENT DOCUMENTS

| 5,157,707 | A | * | 10/1992 | Ohlson | .......................... 378/181 |
| 5,702,389 | A | * | 12/1997 | Taylor et al. | ..................... 606/56 |
| 5,728,095 | A | * | 3/1998 | Taylor et al. | ..................... 606/54 |
| 5,971,984 | A | * | 10/1999 | Taylor et al. | ..................... 606/54 |
| 6,030,386 | A | * | 2/2000 | Taylor | ..................... A61B 17/62 606/54 |
| 6,628,746 | B2 | * | 9/2003 | Eppler et al. | ..................... 378/21 |
| 6,907,629 | B2 | * | 6/2005 | Longton et al. | ................... 5/601 |
| 7,306,601 | B2 | * | 12/2007 | McGrath | ................ A61B 17/62 606/53 |

(Continued)

FOREIGN PATENT DOCUMENTS

| DE | 102 38 579 A1 | 5/2003 |
| DE | 10 2004058450 A1 | 6/2006 |
| WO | WO 2009/121932 | 10/2009 |

OTHER PUBLICATIONS

German office action dated May 2, 2013 for German Application No. 10-2012-216-687.4.

(Continued)

*Primary Examiner* — Allen C. Ho
(74) *Attorney, Agent, or Firm* — Intellectual Property Law Group LLP

(57) ABSTRACT

The invention relates to an apparatus (1) for examining test bodies (P), in particular electronic subassemblies and electronic devices, comprising at least one radiation source (2) for X-raying at least one test body (P), at least one detection unit (3) for detecting radiation (S) emitted by means of the radiation source (2), at least one holding element (4) for holding the at least one test body (P) and for positioning the latter between the radiation source (2) and the detection unit (3), and a movement unit (5), coupled to the holding element (4), for moving the holding element (4), wherein the movement unit (5) is constructed as a parallel-mechanism movement unit.

7 Claims, 1 Drawing Sheet

(56) References Cited

U.S. PATENT DOCUMENTS

| | | | |
|---|---|---|---|
| 7,934,869 B2* | 5/2011 | Ivanov et al. | 378/205 |
| 8,202,273 B2* | 6/2012 | Karidis | A61B 17/62 606/56 |
| 8,257,353 B2* | 9/2012 | Wong | A61B 17/6416 606/59 |
| 8,296,094 B2* | 10/2012 | Harrison | B25J 9/1623 702/150 |
| 8,333,766 B2* | 12/2012 | Edelhauser | A61B 17/62 606/55 |
| 8,377,060 B2* | 2/2013 | Vasta | A61B 17/62 606/56 |
| 8,542,797 B2* | 9/2013 | Roberts | A61N 5/1049 378/65 |
| 2002/0010465 A1* | 1/2002 | Koo | A61B 17/62 606/57 |
| 2003/0191466 A1* | 10/2003 | Austin | A61B 17/62 606/54 |
| 2010/0080349 A1* | 4/2010 | Kalender et al. | 378/37 |
| 2011/0181715 A1 | 7/2011 | Eales | |

OTHER PUBLICATIONS

German 2nd office action dated Oct. 19, 2015 for German Application No. 10-2012-216-687.4.

* cited by examiner

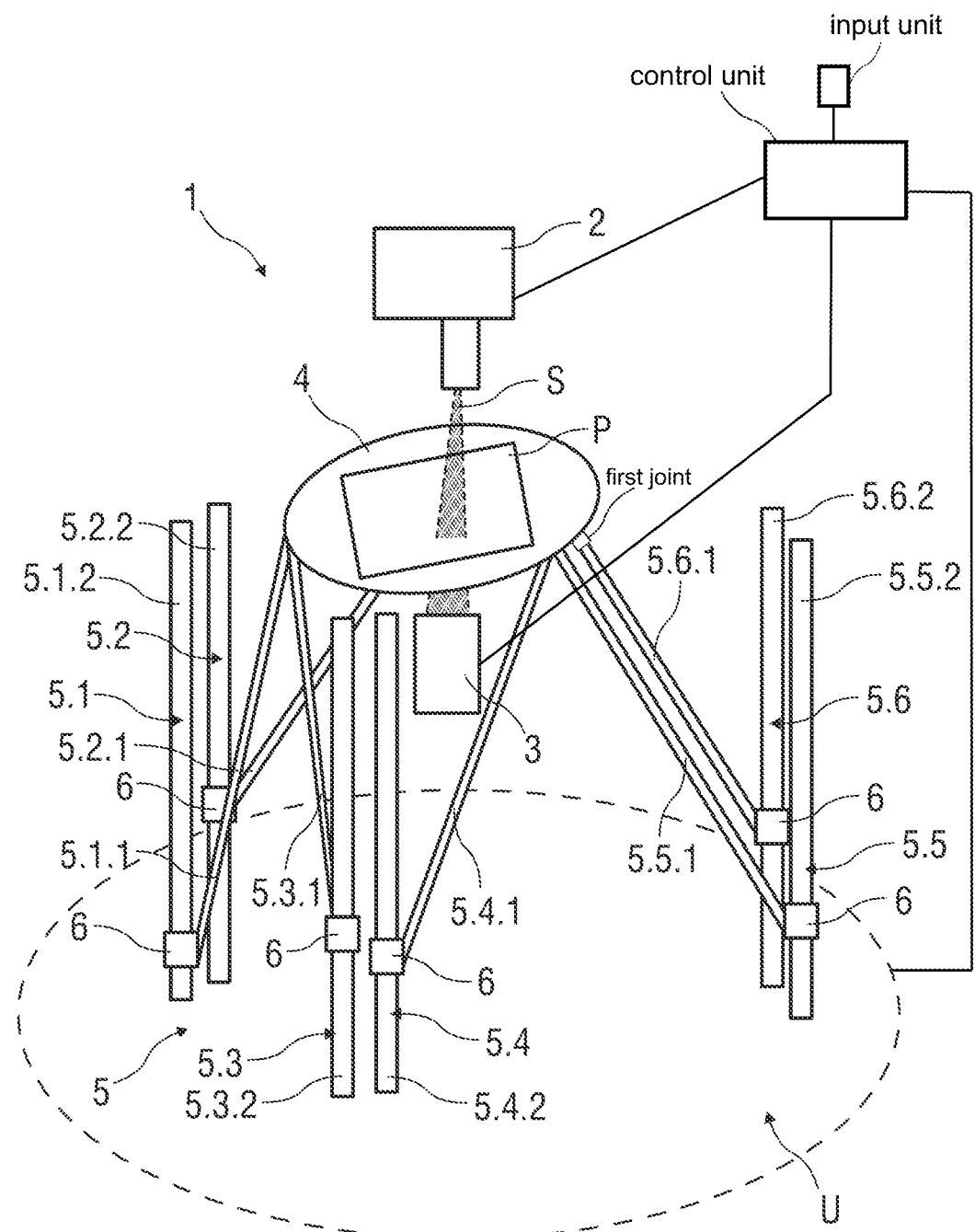

APPARATUS FOR EXAMINING TEST BODIES

CROSS-REFERENCE TO RELATED APPLICATIONS

This application claims priority to German application no. DE 10 2012 216 687.4 filed on Sep. 18, 2012, which is hereby incorporated by reference in its entirety.

BACKGROUND

1. Field of the Invention

The invention relates to an apparatus for examining test bodies, in particular electronic subassemblies and electronic devices.

2. Background Art

Known from the prior art are various apparatuses for examining test bodies, in particular electronic subassemblies and electronic devices.

Furthermore, what are known as manipulators for positioning objects in space are known from the prior art. These manipulators make it possible to position an object with different degrees of freedom. The manipulators are constructed as industrial robots, hexapods or what are known as multi-axis table or portal systems. Furthermore, the manipulators are differentiated with respect to their mechanisms into serial manipulators, such as robots and mills, and parallel manipulators, such as hexapods. On account of their specific properties and parameters, the manipulators are suitable for different areas of application.

In the case of manipulators with serial mechanisms, a plurality of linear movement axes building on one another permit the positioning of an object in several dimensions. Here, each axis is provided for a movement in a defined direction. Furthermore, an additional use of rotary axes is known. An axis carries a further axis in each case, so that any desired positions in space can be set in and as a function of a number of axes.

Manipulators constructed as hexapods with parallel mechanisms are distinguished by an arrangement of six legs or axes, which are attached to a platform that can be moved freely in space. These legs permit positioning of the platform in space. For this purpose, the legs are constructed such that the length thereof can be varied or positions of endpoints of the legs that face away from the platform can be varied.

Irrespective of their design, it is necessary for all apparatuses that these permit predefined absolute and relative repetition accuracies. Here, absolute repetition accuracy is understood to mean the accuracy with which the object can be positioned. The relative repetition accuracy is understood to mean the deviation with which this position can be reproduced. Furthermore, irrespective of their design, the apparatuses have to be matched to a maximum mass and size of the object to be positioned and have a defined number of spatial degrees of freedom in which the object can be positioned. During the optimization of these parameters, i.e. the repetition accuracies, the maximum mass and size of the object and the number of spatial degrees of freedom, these behave contrarily. This means that the improvement of one of the parameters leads to restrictions of the other parameters.

WO 2009/121932 A2 discloses a rotation apparatus which comprises a rotating table having a rotation platform for radiographic, tomographic and laminographic examinations by means of radiation, wherein the rotation platform has a cut-out which is arranged around the axis of rotation. A rotor of the rotation platform or a holder has an XY positioning unit for lateral object positioning with respect to the axis of rotation. In addition, a parallel mechanism system for positioning inclined axes is provided.

Furthermore, US 2011/0181715 A1 discloses an apparatus for examining test bodies with a radiation source.

SUMMARY

The invention is based on the object of specifying an apparatus for examining test bodies that is improved with respect to the prior art.

According to the invention, the object is achieved by an apparatus which has the features specified in claim 1.

Advantageous refinements of the invention are the subject matter of the sub-claims.

The apparatus according to the invention for examining test bodies, in particular electronic subassemblies and electronic devices, comprises at least one radiation source for X-raying at least one test body, at least one detection unit for detecting radiation emitted by means of the radiation source, at least one holding element for holding the at least one test body and for positioning the latter between the radiation source and the detection unit, and a movement unit, coupled to the holding element, for moving the holding element, wherein the movement unit is constructed exclusively as a parallel-mechanism movement unit.

The construction of the movement unit as a parallel-mechanism movement unit particularly advantageously makes it possible for the test body to be arranged and aligned freely in various positions. Thus, the test body can be positioned freely in various test windows, as they are known, and detected by means of the detection unit. In addition, the apparatus according to the invention permits flexible and precise movement of the holding element and thus of the test body with efficient fabrication possibilities.

The construction of the movement unit as a parallel-mechanism movement unit particularly advantageously further permits a large clear space that is transparent to the radiation emitted by the radiation source. Thus, interference with the detection of the test body resulting from the movement unit is avoided and restrictions on the size of the detection area resulting from the movement unit are reduced. This means that, in the viewing direction of the detection unit, no optical obstacles occur—apart from the test body to be examined itself. A series of images detected by means of the detection unit can be incorporated optimally geometrically, so that high-quality images can be produced.

In addition, an optimized alignment of the image axis and of wide-angle and narrow-angle X-ray cones can be implemented, a static arrangement of the radiation source and the detection unit being possible on account of the parallel-mechanism construction of the movement unit. Because of the fact that no mobility of the radiation source and of the detection unit is required, the apparatus is distinguished by an increased service life.

Furthermore, as compared with manipulators with serial mechanisms, the advantage is achieved that no axis has to carry the load of another, so that the moved masses are minimized, which results in a high level of dynamics of the movement unit and thus of the movement of the test body. In addition, as compared with manipulators with serial mechanisms, on account of the parallel-mechanism construction of the movement unit, the result is increased accuracy during the movement, since any errors that occur during the movement appear only linearly, otherwise than in the case of the serial mechanisms. On the other hand, summing of the errors as in the case of the serial mechanisms does not take place, so that the necessary accuracy, in particular in the region of a few micrometers, can be implemented with a highly reduced use of resources.

In addition, the parallel-mechanism movement unit, in particular as compared with serial mechanisms, the production of which is particularly complicated on account of difficult scalability and a high expenditure of energy, can be scaled simply in design terms, mechanically, in control engineering terms and productively. Thus, the apparatus can easily be adapted to changes in the space that is available or to different masses of the test body.

Furthermore, on account of the parallel-mechanism movement unit as compared with serial mechanisms, the apparatus according to the invention is distinguished by particularly low material and production costs. This results from the fact that, in the parallel-mechanism movement unit according to the apparatus according to the invention, all the movement modules are preferably constructed similarly and can thus be produced economically in high numbers. By contrast, in the case of serial mechanisms, each axis has to be adapted with regard to mechanical and electrical design.

A further particular advantage of the apparatus according to the invention resides in the particularly low masses to be moved, on account of the use of the parallel-mechanism movement unit, which results in the possibility of high movement speeds and thus very short examination times of the test body. On the other hand, in particular on account of the axis design, serial-movement mechanisms have significantly higher masses, which, during acceleration and braking, have a detrimental effect on the latter and place a high power requirement on a drive of the movement unit. Thus, as opposed to the serial-movement mechanisms, no defined forces are required on the holding element in the embodiment according to the invention having the parallel-mechanism movement unit, and the apparatus can be adapted simply to the mass of the test body to be examined.

Furthermore, the apparatus according to the invention permits optimization of the space used. A reduction in leg length of the movement unit is possible by restricting a maximum angle of inclination of the holding element to 45°, for example. On account of the possibility of arranging the detection unit in a region between the legs, and the consequent possibility of implementing the radiography method despite the limitation of the angle of inclination, a 360° view of the test body is possible.

In a development of the apparatus, the parallel-mechanism movement unit is a tripod, quadruped, pentapod, hexapod or heptapod having legs of variable length. Such a construction of the movement unit permits a movement of the holding unit that is matched optimally to the respective intended use and thus a movement of the test body into predefined positions with many degrees of freedom. A possible optical magnification can be matched very simply in design terms on account of lengthening or shortening the legs.

In order to optimize the movement with many degrees of freedom into the predefined positions, the legs are in particular fixed to the holding element by means of joints. This permits a free movement of the holding element and thus of the test body during the movement of the movement unit.

According to a refinement of the apparatus, the parallel-mechanism movement unit is a tripod, quadruped, pentapod, hexapod or heptapod, wherein the legs are formed from at least two sub elements in each case. A first sub element is respectively coupled to the holding element by means of a first joint and to a second sub element by means of a second joint. The second sub element is fixed to a base in a fixed location. The second joint is fixed to the second sub element such that it can be displaced on the latter in the longitudinal direction. By means of this refinement, the situation is particularly advantageously achieved in which both the advantage of a parallel-mechanism movement unit and the advantages of a serial-mechanism movement unit are achieved. These advantages result in particular from the simple linear change in the position of a respective end point or leg end point of the first sub element on account of the displacement of the second joint on the second sub element. The possible optical magnification can be adapted very simply in design terms on account of the change in the travel path of the second joint on the second sub element.

In order to increase the movement possibilities and the number of degrees of freedom further, in a possible refinement the parallel-mechanism movement unit comprises a bending arm mechanism. This permits increased variability in the position of the holding element and thus of the test body.

According to an advantageous refinement of the apparatus, at least in the area which is provided for the test body to be arranged, the holding element is formed from a material that is transparent to the radiation emitted by the radiation source, in particular a carbon fiber composite material. Thus, an arrangement of the detection unit on the side of the test body facing away from the radiation source is possible without any complicated optical deflection apparatus, and the holding element does not have a detrimental effect on the method of X-raying the test body implemented by means of the radiation source and the detection unit.

In particular, the radiation source is an X-ray source and the detection unit is designed to detect X-rays. By means of X-rays, the test body can be X-rayed particularly simply, it being possible, according to a development, for precise structural images of the test body to be generated in particular by means of a detection unit formed as an imaging detection unit, which permits exact examination of said test body. Alternatively, other constructions of the radiation source and of the detection unit for implementing a radiographic test are also possible. For example, in this case the radiation source is constructed as a gamma radiation source and the detection unit is designed to detect such gamma radiation.

For the purpose of automation and a resultant simplification of the examination of the test body, in a refinement the movement unit, the radiation source and/or the detection unit can be controlled automatically by means of at least one control unit.

The at least one control unit is preferably coupled to at least one input unit for the pre-definition of a respective direction of movement of the movement unit, which permits simple pre-definition of the movement and/or positioning of the test body that is to be realized.

BRIEF DESCRIPTION OF THE DRAWINGS

Exemplary embodiments of the invention will be explained in more detail below by using a drawing, in which:

FIG. 1 shows a possible exemplary embodiment of the apparatus according to the invention in schematic form.

DETAILED DESCRIPTION OF SPECFIC EMBODIMENTS

The single FIG. 1 shows a possible exemplary embodiment of the apparatus 1 according to the invention for examining test bodies P. The test body P in the exemplary embodiment illustrated is a printed circuit board. As distinct therefrom, the examination of further electronic subassemblies and electronic devices is also possible.

The apparatus 1 comprises a radiation source 2 constructed as an X-ray source for X-raying the test body P. Also provided is a detection unit 3 formed as an imaging detection unit for detecting radiation S emitted by means of the radiation source 2.

Arranged between the radiation source 2 and the detection unit 3 is a holding element 4, which is formed from a carbon fiber composite material that is transparent to the X-rays, in order to hold the test body P and position the latter between the radiation source 2 and the detection unit 3.

A movement unit 5 for moving the holding element 4 is coupled to the holding element 4. The movement unit 5 is constructed as a parallel-mechanism movement unit, the parallel-mechanism movement unit in the exemplary embodiment illustrated being a hexapod, as it is called, having six legs 5.1 to 5.6.

The legs 5.1 to 5.6 are each formed from two sub elements 5.1.1, 5.2.1, 5.3.1, 5.4.1, 5.5.1, 5.6.1, 5.1.2, 5.2.2, 5.3.2, 5.4.2, 5.5.2, 5.6.2. First sub elements 5.1.1, 5.2.1, 5.3.1, 5.4.1, 5.5.1, 5.6.1 are respectively coupled to the holding element 4 by means of a first joint, not shown.

Furthermore, the first sub elements 5.1.1, 5.2.1, 5.3.1, 5.4.1, 5.5.1, 5.6.1 are each coupled by means of a second joint 6 to a second sub element 5.1.2, 5.2.2, 5.3.2, 5.4.2, 5.5.2, 5.6.2. The second sub elements 5.1.2, 5.2.2, 5.3.2, 5.4.2, 5.5.2, 5.6.2 are fixed to a base U in a fixed location and formed as a spindle axis, wherein the second joints 6 can each be displaced in the longitudinal direction on the second sub elements 5.1.2, 5.2.2, 5.3.2, 5.4.2, 5.5.2, 5.6.2 formed as a spindle axis. For this displacement, in a manner not specifically illustrated, the second joints 6 each comprise drive units which can be controlled independently of one another.

Alternatively, in a manner not specifically illustrated, the legs 5.1 to 5.6 are formed as variable-length legs.

The movement unit 5 constructed as a hexapod makes it possible for the test body P to be positioned very freely in space. In addition, as a result of the design, the structure of a hexapod produces a free space between the legs 5.1 to 5.6 which, in the apparatus 1 according to the invention, can be used in an application-based manner, in which the detection unit 3 is arranged in said space in such a way that it is not influenced by constituent parts of the movement unit 5.

In a manner that is not specifically illustrated, the movement unit 5, the radiation source 2 and the detection unit 3 can be controlled automatically by means of at least one control unit. Also particularly preferably, in a manner likewise not specifically illustrated, at least one input unit is coupled to the control unit, the input unit being provided for the pre-definition of a respective direction of movement of the movement unit 5. The input unit is in particular a six-dimensional input device having three rotational and three translational degrees of freedom, in particular what is known as a space mouse.

In order to examine the test body P, the latter is moved by means of the movement unit 5 into different defined positions, radiography of the test body P by means of the radiation S and detection of an image of the test body P by means of the detection unit 3 being carried out in each position, preferably sequentially. On account of the possibility of arranging the test body P outside the area of the legs 5.1 to 5.6 of the movement unit 5, the apparatus 1 is preferably not restricted to specific sizes of the respective test body P. The apparatus 1 permits radiography and examination of the test body P from various perspectives, in particular a complete 360° view thereof. Oblique radiography of the test body P is also possible.

LIST OF ELEMENTS

1 Apparatus
2 Radiation source
3 Detection unit
4 Holding element
5 Movement unit
5.1 Leg
5.1.1 First sub element
5.1.2 Second sub element
5.2 Leg
5.2.1 First sub element
5.2.2 Second sub element
5.3 Leg
5.3.1 First sub element
5.3.2 Second sub element
5.4 Leg
5.4.1 First sub element
5.4.2 Second sub element
5.5 Leg
5.5.1 First sub element
5.5.2 Second sub element
5.6 Leg
5.6.1 First sub element
5.6.2 Second sub element
6 Second joint
P Test body
S Radiation
U Base

What is claimed is:

1. An apparatus for examining test bodies, in particular electronic subassemblies and electronic devices, comprising:
   at least one radiation source for radiating x-rays toward at least one test body;
   at least one detection unit for detecting x-rays radiated by the at least one radiation source;
   at least one holding element for holding the at least one test body and for positioning the at least one test body between the at least one radiation source and the at least one detection unit;
   a movement unit, coupled to the at least one holding element, for moving the at least one holding element; and
   a base;
   wherein the movement unit is constructed exclusively as a parallel-mechanism movement unit;
   wherein the parallel-mechanism movement unit is a tripod, quadruped, pentapod, hexapod, or heptapod that comprises legs, wherein each leg of the legs comprises at least two sub elements, wherein the at least two sub elements comprise a first sub element and a second sub element, wherein the first sub element includes a first joint and a second joint;
   wherein the first sub element is respectively coupled to the at least one holding element by the first joint and to the second sub element by the second joint;
   wherein the second sub element is fixed to the base in a fixed location and the second joint is fixed to the second sub element such that the second joint can be displaced on the second sub element in the longitudinal direction.

2. The apparatus as claimed in claim 1, wherein at least in the area which is provided for the at least one test body to be arranged, the at least one holding element comprises a material that is transparent to the x-rays radiated by the at least one radiation source.

3. The apparatus as claimed in claim 1, wherein at least in the area which is provided for the at least one test body to be arranged, the at least one holding element comprises a carbon fiber composite material.

4. The apparatus as claimed in claim 1, wherein the at least one radiation source is an X-ray source.

5. The apparatus as claimed in claim 1, wherein the at least one detection unit is an imaging detection unit.

6. The apparatus as claimed in claim 1, further comprising at least one control unit, wherein the movement unit, the at least one radiation source and/or the at least one detection unit can be controlled automatically by the at least one control unit.

7. The apparatus as claimed in claim 6, further comprising at least one input unit coupled to the at least one control unit for the pre-definition of a respective direction of movement for the movement unit.

* * * * *